United States Patent [19]

Diamond

[11] Patent Number: 4,511,329
[45] Date of Patent: Apr. 16, 1985

[54] MOISTURE CONTROLLING LINGUAL DENTAL MIRROR

[76] Inventor: Michael K. Diamond, 86 Milburn La., Roslyn, N.Y. 11577

[21] Appl. No.: 574,259

[22] Filed: Jan. 26, 1984

[51] Int. Cl.³ .............................. A61C 1/00; A61C 3/00
[52] U.S. Cl. ........................................ 433/31; 433/140
[58] Field of Search ......................... 433/30, 31, 93, 94, 433/140; 128/12

[56] References Cited

U.S. PATENT DOCUMENTS

| | | | |
|---|---|---|---|
| 2,823,455 | 2/1958 | Sprague | 433/93 |
| 2,862,299 | 12/1958 | Reiter | 433/31 |
| 2,937,445 | 5/1960 | Erickson | 433/93 |
| 4,179,815 | 12/1979 | Hoffman | 128/12 |

*Primary Examiner*—Robert Peshock

[57] ABSTRACT

A dental instrument for viewing the lingual surface of dentition and also providing moisture control as a saliva ejector and serving as a tongue holder and support for a cheek retractor. The instrument includes a base wall on which is placed a mirror and a pair of laterally extending side walls which can be used as rest blocks for the teeth during the dental procedure. A channel is formed internally of the instrument with a plurality of aspirator holes in flow communication with the channel. Outlet ports are provided also in flow communication with the channel to which can be connected tubing from a suction source. The dental instrument is positioned in the mouth so as to span the mouth cavity rearwardly of the upper and lower dentition and is self holding so that it can reflect the lingual surface of the dentition without being held manually in place.

24 Claims, 15 Drawing Figures

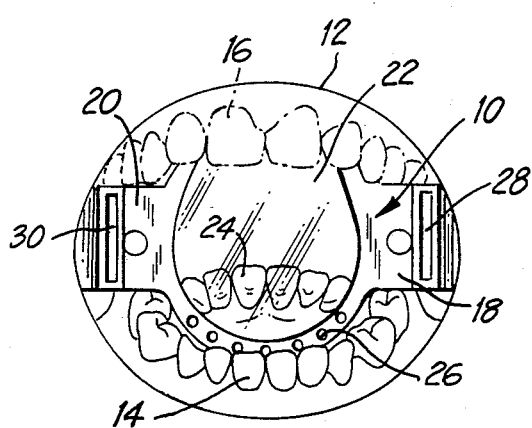
FIG. 1
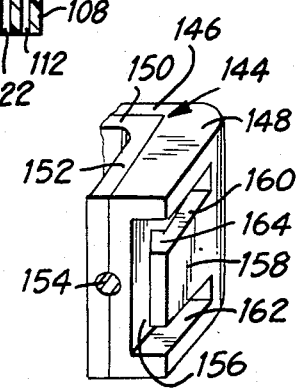
FIG. 2
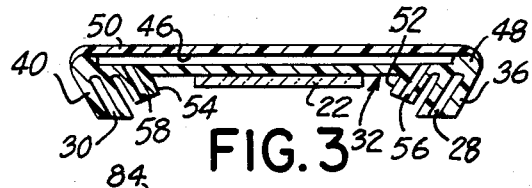
FIG. 3
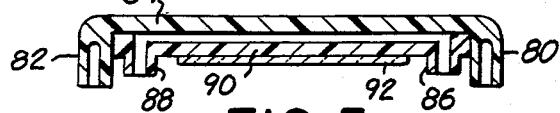
FIG. 5
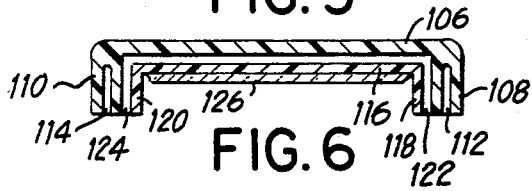
FIG. 6
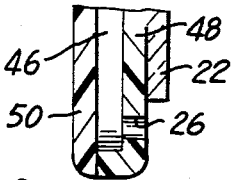
FIG. 4
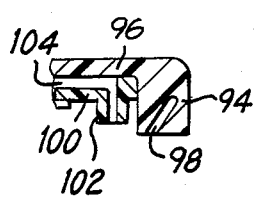
FIG. 7
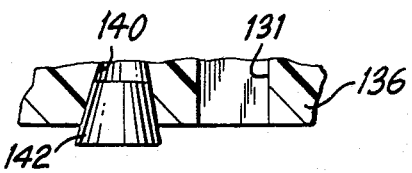
FIG. 9
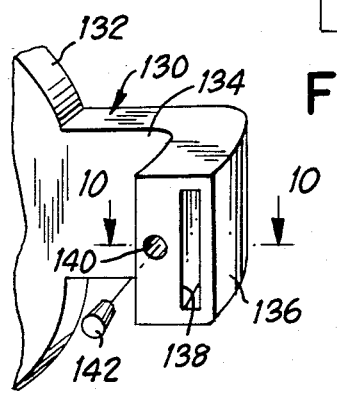
FIG. 8
FIG. 10

MOISTURE CONTROLLING LINGUAL DENTAL MIRROR

BACKGROUND OF THE INVENTION

This invention relates to dental instrumentation, and more particularly to a dental mirror for viewing the lingual surface of dentition, which also provides the necessary moisture control and tongue holding functions required for proper dental procedures.

In most dental procedures, a mirror is required so the dentist can view the various surfaces of the dentition. Typically, an instrument having a mirrored surface is hand held by the dentist or a dental assistant, while the procedures are conducted. However, such hand held mirror prevents the dentist from utilizing two hands in conducting the particular dental procedure. Even when a dental assistant is utilized to hold the mirror, it crowds the dental work area and adds difficulty to efficient dental work.

The most difficult surface of dentition which is to be viewed, is the lingual surface of the lower teeth. Special shaped and curved mirrored instruments are generally needed to view such surface and most of these require manual holding during the course of the dental procedures.

Additional requirements for conducting dental procedures involve moisture control and tongue restraining. Various types of saliva ejectors are utilized for providing the necessary moisture control of the dental area. Most of these utilize tubing having an aspirator at its distal end which is placed in a mouth cavity and is connected to a vacuum source. The ejector evacuates fluids from the dental area to maintain a clear and dry work field. However, such systems mean extra equipment and apparatus depending from the patient's mouth, and again crowds the dental work area making it more difficult to properly conduct dental procedures.

The restraining of the tongue also presents a problem for keeping a clear dental work area. Because of the natural instinct to project the tongue forwardly, many types of dental instruments are utilized for restraining the tongue and at the same time protecting it from damage should it enter into the work area. Again, however, use of tongue holding apparatus further crowds the mouth cavity and restricts the dental work area making it further cumbersome to obtain a clear field of work.

Other problems in carrying out dental procedure also involve the use of apparatus which further crowds the dental work area. For example, when work must be carried out on the rearward parts of dentition, it is desirable to spread the cheeks to prevent the patient from closing in on the work area. Cheek retractors can be utilized to spread the mouth opening. However, these again add additional apparatus to the mouth which further crowds the area of dental work.

Other problems relate to the resting of the dentition in the case of a long dental procedure. Where the mouth must be maintained in an open position for a considerable length of time, the patient is under a continuous strain to keep the jaws open and the dentition of the upper and lower teeth spread apart. Rest blocks are frequently utilized to space the dentition apart and at the same time allow the patient to relax while maintaining an optimum opening for the dental procedure.

However, again additional apparatus must be utilized which further crowds the dental area. Accordingly, while various apparatus is available for aiding the dentist in the conduct of the various dental procedures, the necessity for utilizing a number of different apparatus for each procedure is problematic. The use of the various apparatus crowds the dental area and prevents the dentist from sufficient access to the dentition being worked on. Also, it requires additional use of hands which limits the ability of the dentist to give total dedication to the dental procedure without concern for the peripheral apparatus. Additionally, it also adds cost since each of the apparatus requires separate manufacture and must be purchased individually for the particular use to which it is designed.

SUMMARY OF THE INVENTION

Accordingly, it is an object of the present invention to provide a dental instrument which avoids the aforementioned problems of prior art devices.

A further object of the present invention is to provide a dental instrument for viewing the lingual surface of dentition.

A further object of the present invention is to provide a dental instrument for viewing the lingual surface of the lower dentition without the instrument being manually held by the dentist or dental assistant.

Yet another object of the present invention is to provide a dental mirror for viewing the lingual surface of dentition, which is self standing without the need of it being held by the dentist.

Still a further object of the present invention is to provide a dental instrument for viewing the lingual surface of dentition, which also provides the necessary moisture control for the work area.

Another object of the present invention is to provide a dental instrument which combines a lingual mirror and a saliva ejector.

Another object of the present invention is to provide a dental instrument which can be used for viewing the lingual surface of dentition and also serves to restrain the tongue from the work area.

Yet a further object of the present invention is to provide a dental mirror for viewing the lingual surface of dentition which also includes rest blocks for the patient's dentition during dental manipulation.

Still another object of the present invention is to provide a dental instrument which is self supporting in the patient's mouth and permits viewing of the lingual surface of dentition, restrains the tongue, provides rest blocks for the dentition, and serves as a saliva ejector for maintaining moisture control of the work area.

Another object of the present invention is to provide a dental instrument for viewing the work surface of dentition which can also serve to support cheek retractors so as to maintain a proper mouth cavity opening for dental manipulation.

A further object of the present invention is to provide a dental instrument for viewing the lingual surface of dentition which permits replacement of the mirrored surface for each usage.

Briefly, in accordance with the present invention, there is provided a dental instrument which can be used to view the lingual surface of the dentition. The instrument includes a base member which is positioned in the mouth from top to bottom so as to span the mouth cavity rearwardly of the upper and lower dentition. On a forward surface of the base member, there is provided a reflective device, such as a mirror. The base member serves to restrain the tongue from entering into the work area. A pair of wall members laterally extend on either side of the base member to maintain the upper and lower dentition in spaced relationship. At the same time, the wall members provide rest blocks for supporting the dentition during dental manipulations.

A channel is associated with the base wall member and includes a plurality of input suction holes in flow communication with the channel. An outlet is also in flow communication with the channel. An external vacuum source can be connected to the outlet by means of a flexible tube. In this manner, the dental instrument also provides moisture control of the dental area by serving as a saliva ejector.

In an embodiment of the invention, the wall members include slots for insertion of cheek retractors to permit maintaining a proper mouth opening for the dental procedure.

The reflective device, such as the mirror, can be made removable from the base wall so that a new mirror surface can be applied for each patient.

The aforementioned objects, features and advantages of the invention will, in part, be pointed out with particularity and will, in part, become obvious from the following more detailed description of the invention, taken in conjunction with the accompanying drawings, which form an integral part thereof.

BRIEF DESCRIPTION OF THE DRAWING

In the drawings:

FIG. 1 is a vertical schematic view of the mouth cavity showing positioning of the dental instrument of the present invention;

FIG. 2 is an exploded perspective view of the various parts of the dental instrument in accordance with an embodiment of the present invention;

FIG. 3 is a cross sectional view taken along lines 3—3 of FIG. 2;

FIG. 4 is a cross sectional view taken along lines 4—4 of FIG. 2;

FIG. 5 is a cross sectional view similar to that shown in FIG. 3 and showing an alternate embodiment of construction of the present invention;

FIG. 6 is a cross sectional view similar to that shown in FIGS. 3 and 5 and showing yet a further embodiment of construction of the present invention;

FIG. 7 is a fragmentary cross sectional view similar to that shown in FIGS. 3, 5 and 6 and showing yet a further construction of the present invention;

FIG. 8 is a fragmentary perspective view showing an alternate embodiment of the side wall member of the dental instrument;

FIG. 9 is a perspective view similar to that shown in FIG. 8 showing a modified embodiment of the side wall member;

FIG. 10 is a cross sectional view taken along line 10—10 of FIG. 8;

In the various figures of the drawings, like references characters designate like parts.

DESCRIPTION OF THE PREFERRED EMBODIMENT

Figure 11:
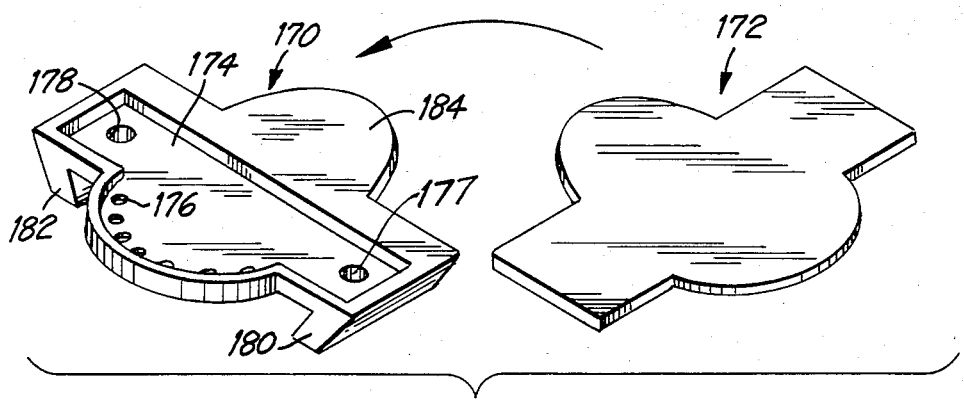
FIG. 11 is an exploded perspective view showing the parts of the dental instrument in accordance with the present invention.

Referring now to FIG. 1, the dental instrument of the present invention is shown generally at 10 and is schematically shown positioned within a mouth cavity 12. It should be noted, that the instrument 10 is vertically oriented within the mouth cavity, having its lower portion situated behind the lower dentition 14 and its upper end situated behind the upper dentition 16. Specifically, the dental instrument 10 is typically located behind the incisor teeth as well as the bicuspid teeth, and can be positioned adjacent the molar teeth area.

The instrument 10 includes side portions 18, 20 which serve to space apart the rear dentition, typically the molars. The molars can also close onto these side members 18, 20 whereby they act as rest blocks allowing the patient to relax during the dental procedure while maintaining the necessary optimum opening for such procedure.

On the front surface of the dental instrument is provided a reflective surface, such as a mirror 22. As will be evident, the device is self retained within the mouth cavity by having its upper and lower ends held between the palate and the bottom mouth cavity Also, the use of the side portions 18, 20 aid in maintaining the instrument stable and vertical within the mouth cavity. When positioned as shown, the lingual surface of the lower dentition 14 is reflected in the mirror 22 as shown by the reflection 24. In this manner, the dentist can place the dental instrument in the mouth cavity and without the requirement of holding the instrument manually, he will be able to view the lingual surface of the dentition.

It will be noted in FIG. 1, that there are provided a plurality of aspirating holes 26 at the lower surface of the dental instrument. As will hereinafter be explained, these serve to control the moisture in the dental work area by aspirating the saliva. The dental instrument will be connected to a suitable source of a vacuum for providing a saliva ejector in the mouth area.

As will also be apparent, since the dental instrument is positioned forward of the tongue, it serves as a tongue holder by restraining the tongue from entering into the dental work area which is forward of the dental instrument.

As a result, it will be apparent that the device as shown in FIG. 1 serves as a dental mirror for viewing the lingual surface, and simultaneously can be used as a saliva ejector, tongue holder, and rest block for the dentition. As will be explained hereinafter, the side slots 28, 30 are available for insertion of cheek retractors which can spread the mouth opening to a desired optimum amount for the dental procedure.

Referring now to FIGS. 2, 3 and 4, the dental instrument 10 is shown to include a substantially oval base wall member 32 on which is placed an oval mirror 22. The mirror itself can be a separate member which is applied to the surface of the base 32, or alternately can actually be molded into the surface 32. As will hereinafter be explained, the mirror can be made replaceable and a new mirror can be applied for each patient.

Laterally extending from either side of the base member 32 are the side wall members 18 and 20. The side wall portion 18 includes an L-shaped configuration having the rear wall 34 with the forwardly projecting section 36. The slot 28 is formed into the forwardly projecting wall section 36. The side wall member 20 likewise includes the rear portion 38 with the forwardly projecting section 40 in which is formed the slot 30.

The base wall 32 together with the side wall sections 18, 20 can be integrally molded of single construction. In this manner, the thickness of the base wall 32 with the side wall sections 34, 38 can be uniform. The forwardly projecting sections 36, 40, can be made slightly thicker. The height of the side wall portions 18, 20 is less both at the upper and lower ends than the oval base member 32. The oval shape of the base member is such as to have its lower end 42 suitable for fitting into lower mouth cavity behind the incisor dentition. The upper end 44 can suitably fit against the palate without causing any discomfort. The height of the side wall portions 18, 20 is such as to maintain the upper and lower dentition in spaced relationship but yet permitting the molar teeth of the upper and lower dentition to rest on the top and bottomsurfaces of these side portions.

As can best can be seen in FIGS. 3 and 4, internally of the base wall, as well as extending to the side wall portions, there is included a channel 46. Typically, the channel can be defined by making the dental instrument of two piece construction, namely the front wall 48 and the rear wall 50 whereby the channel 46 is defined therebetween. Various embodiments of such construction will be hereinafter described in connection with FIGS. 11-13.

The aspirator holes 26 are spaced along the lower part of the base wall member beneath the mirror 22. As noted in FIG. 4, these are in flow communication with the channel 46 whereby saliva which is sucked into the aspirator holes 26 is brought into the channel 46.

Projecting from the front surface of the side walls 34, 38 are the nipples 52, 54. These include the respective openings 56, 58 which feed into the channel 46. As is shown in FIG. 2, suitable flexible hose 60 having an adaptor 62 at its end, can be placed over the nipple 52 or 54. With the hose 60 connected to a suitable source of vacuum, saliva will be sucked into the aspirator hole 26, flow through the cahnnel 46, and be ejected through the flexible hose 60.

Although only one nipple need be used, a nipple is provided in each side to facilitate connection of the hose depending upon which area of the mouth is being worked on. This permits connection of the hose away from the work area. When one of the nipples is being used, an appropriate cap 64 is provided to close off the other nipple so as to maintain the vacuum within the channel.

As shown in FIG. 2, cheek retractors 66, 68 can be removably inserted into respective slots 28, 30, in order to spread apart the mouth cavity to provide sufficient opening for dental procedures. The cheek retractors are arcuate in shape having a substantially U-shaped cross sectional area including the opposing side walls 70, 72 and the interconnecting wall 74. Projecting from one of the side walls 72, is a tab 76 which is removably received within the slot 28, 30. The tab 76 can be smooth or can include a channel 78 therein for engaging a corresponding lip in the slot 28,30 as will hereinafter be explained. Alternately, it can be flat and just wedge into the slot.

As was shown in FIGS. 2 and 3, the inwardly projecting walls 36, 40 at the lateral ends of the dental instrument were inwardly directed. Similarly, the nipples 52, 54 were inwardly angled. However, other configurations can be utilized. For example, as shown in FIG. 5, the inwardly projecting end walls 80, 82 are substantially perpendicular to the back wall 84. Similarly, the coupling nipples 86, 88 are also substantially perpendicular to the back wall 84. In the construction shown in FIG. 3, it should be noted that the side portions including the inwardly directed end portions were integrally formed with the forward wall of the base member, and the back wall 50 serve to close off the channel 46. In the construction shown in FIG. 5, on the contrary, the inwardly projecting end walls 80, 82 are integrally formed with the back wall 84. The front wall 90 supporting the mirror 92 serves as the closure member to the front wall. The nipples 86, 88 are formed integrally with the front wall 90.

FIG. 7 shows a combination of the embodiments of FIG. 3 and FIG. 5. Specifically, the end wall section 94 is substantially perpendicular to the rear wall 96. However, the slot 98 accommodating the cheek retractor is angularly formed into the side wall 94. The forwardly projecting end wall 94 is integrally formed with the back wall 96. The front wall 100, supports the nipple 102, and acts as a closure member for the channel 104 enclosed therebetween.

FIG. 6 yet provides an alternate embodiment of construction. In this embodiment, the back wall 106 is integrally formed with the inwardly projecting end walls 108, 110. The end walls 108, 110 are substantially perpendicular to the back wall as are the slots 112, 114 for receiving the cheek retractors. The front wall 116 has inwardly directed arms 118, 120 which form the outlets 122, 124 from the vacuum ejector in conjunction with the walls on the end sections 108, 110. The mirror 126 is formed on the front surface of the front wall 116. Perspective views of the embodiment shown in FIGS. 3, 5 and 6 will be subsequently described in connection with FIGS. 11, 12, and 13. Referring now to FIG. 8, there is shown an alternate embodiment of construction showing a side section 130 extending from a base wall 132. The side section includes a lateral wall section 134 and a forward projecting section 136 in which there is provided a slot 138 for receiving the cheek retractor. Rather than utilize a nipple for coupling to the suction tube, there is provided a receptacle plug 140 in which the end of the vacuum tube can be inserted. As shown in FIG. 10, the receptacle plug 140 has tapered side walls so as to provide a tight fit upon insertion of the suction tube. Since two such plug receptacles 140 would be provided, one on either end section, there is also provided a plug 142 which can close off the particular receptacle not being utilized by the vacuum tube so as to maintain the vacuum within the existing channel. Each of the plug receptacles 140 would be in flow communication with an internal channel to which would be connected the aspirator apertures for sucking in the saliva.

FIG. 9 shows an alternate construction of the end section wherein the section 144 includes a back wall 146 and a forwardly directed end wall 148. The front wall 150 in this case also includes a forwardly projecting wall section 152 which sandwiches against the section 148. The plug receptacle 154 for receiving the vacuum tube is defined by semi-circular channels formed respectively in the wall sections 152, 148, as will be shown hereinafter in connection with FIG. 13.

The slot 156 for receiving the cheek retractor has an outer wall 158 having an upper and lower channel 160, 162 formed therein, so as to permit the wall 158 to flex. An inwardly directed lip 164 terminates at the distal end of the wall 158.

Figure 15:
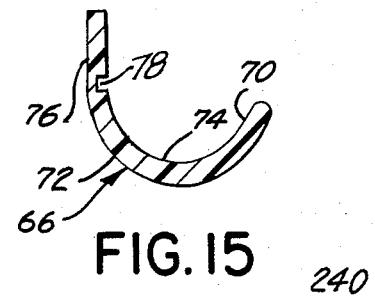
FIG. 15 is a cross sectional view taken along lines 15—15 of FIG. 2.

As best shown in FIG. 15, and as heretofore described also in connection with FIG. 2, the tab 76 at the end of the cheek protractor can include a notch 78 which will engage the lip 164 whereby the cheek retractor 66 will be locked in place and will not slip out.

Referring now to FIG. 11, the construction of the dental instrument heretofore shown in connection with FIGS. 2, 3 and 4 will be described. The instrument is formed of a front section 170 and a rear closure member 172. The front section includes the recessed portion 174 which defines therein the channel for the vacuum aspirator. The holes 176 are used to aspirate the saliva which will flow into the channel 174. The outlets 176, 178 are used for connection to the vacuum tube for ejection of the saliva. The rear wall 172 closes off the channel and covers the entire back surface.

In the embodiment shown in FIG. 11, the side walls with the forward projecting end walls 180, 182 are integrally formed of single construction with the base member 184.

Figure 12:
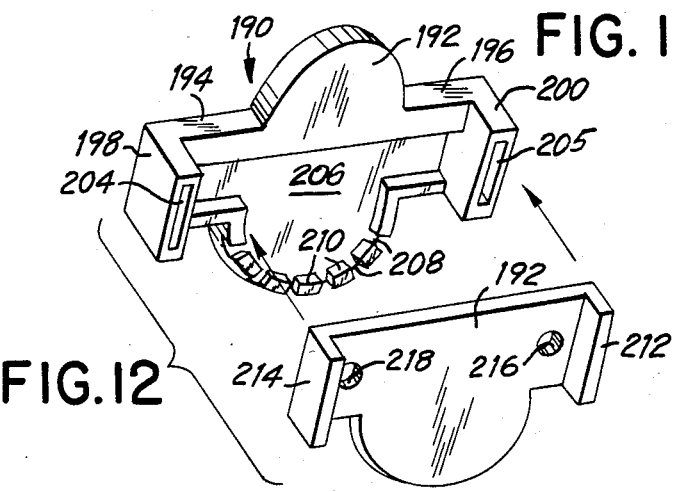
FIG. 12 is an exploded perspective view similar to that shown in FIG. 11 showing an alternate construction of the parts of the dental instrument of the present invention.

In the embodiment shown in FIG. 12, the construction of the instrument will result in a cross section substantially corresponding to that shown in FIG. 5. In this case, the main construction is formed from the back wall member 190 with the front portion 192 serving only to close off the channel. The back wall section 190 supports the base member 192 and the side members 194, 196 with the forward projecting end members 198, 200. The slots 202, 204 for insertion of the check retractors are provided in the end walls 198, 200.

The channel 206 is defined by a recessed portion formed within this section 190. Rather than providing aperture holes for aspiration of the saliva, cut out slots 208 are formed in the bottom peripheral wall 210 surrounding the channel 206.

The front section 192 includes side walls 212, 214, which abut against the sections 198, 200 and close off the channel. The outlets 216, 218 can be either nipples or receptacles for connection to the suction tube to serve as the saliva ejector.

Figure 13:
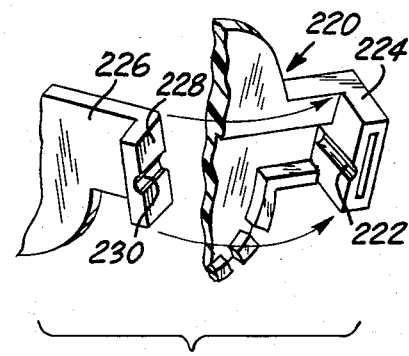
FIG. 13 is a fragmentary perspective view similar to that shown in FIGS. 11, and 12 and showing yet a further construction of the dental instrument in accordance with the present invention.

FIG. 13 shows the two sections which can be utilized to form the construction substantially similar to that shown in FIGS. 6 and 9. In this case, the rear wall section 220 again includes substantially most of the structure. However, rather than have the entire outlet defined within the front or rear section, it is formed between the two sections. Specifically, a semi-circular groove 222 is defined in this end section 224 of the rear construction 220. In the front cover member 226 there is again provided a side wall 228 which abuts against the end wall 224. A corresponding semicircular groove 230 is provided which mates with the groove 22 so as to define therebetween the necessary receptacles for the suction tube.

Figure 14:
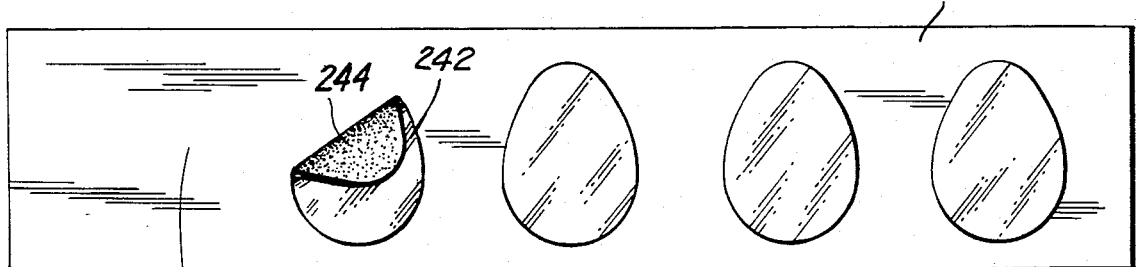
FIG. 14 is an elevational view showing a strip of material from which replacable mirrors can be taken for use with the dental instrument of the present invention.
Figure 14:
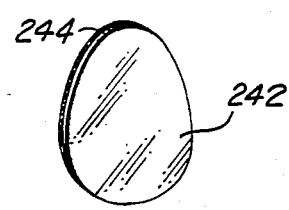

The particular mirror described heretofore, can be permanently secured onto the instrument. Alternately, it can be removably connected so as to be disposable and replaced for each subsequent use. As shown in FIG. 14, the mirrors can be supplied on a continuous strip 240 with each of the mirrors 242 individually spaced apart.

Each mirror can include an adhesive self sticking backing 244 which serves to retain the mirror on the strip 240. When removed from the strip, it can then be placed onto the base wall of the dental instrument and used for the particular patient. Subsequently the mirror can be removed and discarded while the dental instrument itself is resterilized for subsequent use at which time another mirror will be added.

Although the particular shape of the mirrors have been shown as being oval in shape to conform to the shape of the base wall, it should be understood that other such shapes could be similarly utilized so as to provide the best viewing of the lingual surface. Also, the particular shapes of the structures could also be modified so as to provide the best manufacturing capabilities for lowest cost and best manipulation by the dentist.

Although the device has been shown as being vertically oriented in the mouth, it should be appreciated that it could also be obliquely positioned. The important aspect is that it be positioned behind the teeth and situated in the space from top to bottom of the mouth cavity.

There has been disclosed heretofore the best embodiments of the invention presently contemplated. However, it is to be understood that various changes and modifications may be made thereto without departing from the spirit of the invention.

I claim:

1. A dental instrument for viewing the lingual surface of the lower dentition comprising:
   a rigid planar base member for positioning in a substantially vertical orientation from top to bottom of the mouth so as to vertically span the mouth cavity rearwardly of the upper and lower dentition and supporting a planar reflective means on a forward surface thereof, for reflecting the lingual view of the lower dentition while precluding the tongue from entering the dental work area, and
   a pair of wall members laterally extending on either side of said base member for maintaining the upper and lower dentition in spaced relationship and for providing rest blocks for the dentition.

2. A dental instrument as in claim 1 and comprising channel means associated with said base wall member, a plurality of input suction holes formed into lower edge of said base wall member in flow communication with said channel means, and outlet coupling means in flow communication with said channel, for connection to an external vacuum source, whereby said dental instrument serves as a saliva ejector.

3. A dental instrument as in claim 1, and comprising a cheek retractor coupled to each of said wall members.

4. A dental instrument as in claim 2, wherein said base member comprises mating front and rear walls and defining an internal channel therebetween, said cavity serving asthe channel means.

5. A dental instrument as in claim 4, wherein said input suction holes are formed in one of said front and rear walls, and are in flow communication with said internal cavity.

6. A dental instrument as in claim 4, wherein one of said front and rear walls supports a peripheral edge wall at least partially surrounding said internal cavity and spaced between said front and rear walls, and wherein said input suction holes comprise a slot formed into said edge wall.

7. A dental instrument as in claim 2, wherein said channel means extends to said wall members and wherein said outlet coupling means comprises a nipple projecting from at least one of said wall members, the end of a vacuum tubing coupling to said nipple.

8. A dental instrument as in claim 2, wherein said channel means extends to said wall members, and wherein said coupling means comprises a female receptacle formed in at least one of said wall members, the end of a vacuum tubing plugging into said receptacle.

9. A dental instrument as in claim 8, wherein said receptacle is inwardly tapered to provide a tight fit for the tubing.

10. A dental instrument as in claim 2, and comprising an outlet coupling means on each lateral side of said instrument, and comprising plug means for closing off one of said coupling means while the other is in use.

11. A dental instrument as in claim 1, wherein each of said wall members comprise an L-shaped configuration having one wall substantially parallel with said base member and the other wall forwardly projecting therefrom.

12. A dental instrument as in claim 11, wherein said forwardly projecting wall members are inwardly angled.

13. A dental instrument as in claim 11, and comprising a slot formed into each of said forwardly projecting walls for respectively receiving a tab of a cheek retractor.

14. A dental instrument as in claim 13 and comprising a flexible side wall on one side of each of said slots to facilite entry of the cheek retractor tab into the slot.

15. A dental instrument as in claim 14, and comprising a lip on each of said flexible side walls projecting into its respective slot for engaging a mating groove on the cheek retractor tab to lock the tab into the slot.

16. A dental instrument as in claim 1, wherein said base member is substantially flat and oval in shape, and said wall members are of L-shaped configuration having a first flat wall section integrally extending laterally from said base member and a second wall section integrally extending forwardly from said first wall section, said first and second wall sections being of uniform height and shorter at both its top and bottom than said base member.

17. A dental instrument as in claim 16, wherein said base member and said first wall sections are of uniform thickness, and said second wall sections are of greater thickness than said first wall sections.

18. A dental instrument as in claim 1, and comprising a removable mirror for connecticnto the forward surface of said base member.

19. A dental instrument as in claim 18, and comprising a strip of backing material and a plurality of removable mirrors coupled thereto for selective disposable coupling onto said base member.

20. A combination lingual mirror and saliva ejector for dental use, comprising:
   a rigid planar wall member supporting a planar reflective means on one surface thereof;
   a channel associated with said wall member, a plurality of holes formed at the bottom edge of said wall member in flow communication with said channel, and an outlet means coupled to said channel for connection to a suction source, and
   retention means for retaining said wall member in a mouth cavity in a substantially vertical orientation extending between the top and bottom of the mouth and positioned rearwardly of said upper and lower dentition, for reflecting the lingual view of the lower dentition.

21. The combination as in claim 20, wherein said wall member comprises a substantially oval configuration corresponding to the mouth cavity.

22. The combination as in claim 20, and comprising a bite block laterally extending on either side of said wall member onto which the rear dentition can rest.

23. The combination as in claim 20, wherein said one surface supporting said reflective means is fowardly facing, and comprising a substantially flat rear surface for precluding the tongue from entering the work area.

24. The combination as in claim 22, and comprising a pair of removable cheek retractors respectively coupled to said bite blocks.

* * * * *